United States Patent [19]

Romano

[11] 4,135,503
[45] Jan. 23, 1979

[54] ORTHOPEDIC DEVICE

[76] Inventor: Nicholas A. Romano, 30 Pasadena Ave., North, St. Petersburg, Fla. 33710

[21] Appl. No.: 757,073

[22] Filed: Jan. 5, 1977

[51] Int. Cl.² ............................................. A61F 5/02
[52] U.S. Cl. ..................................... 128/78; 128/118
[58] Field of Search ......... 128/78, 75, 84 R, DIG. 20, 128/95, 118, 522; 5/368, 369; 33/174 G

[56] References Cited
U.S. PATENT DOCUMENTS

| | | | |
|---|---|---|---|
| 718,408 | 1/1903 | Wetmore | 128/118 |
| 1,646,590 | 10/1957 | Mildenberg | 128/DIG. 20 |
| 3,717,143 | 2/1973 | Johnson | 128/78 |
| 3,974,827 | 8/1976 | Bodeen | 128/DIG. 20 |

*Primary Examiner*—Robert W. Michell
*Assistant Examiner*—Michael H. Thaler

*Attorney, Agent, or Firm*—Duckworth, Hobby, Allen & Pettis

[57] ABSTRACT

An orthopedic device designed and configured to provide ambulatory traction to specific levels of the spine of a human wherein an inflatable bladder is affixed between a rigid base plate and an apertured template plate so as to extend outwardly therefrom to engage the back portion of a patient and provide predetermined specifically directed pressure to predetermined portions of the spine. The traction apparatus which includes the bladder, template plate and base plate are removably mounted to a belt having both a latex portion causing expandable support when placed in surrounding relation to the patient as well as brace strapping which is relatively unyieldable so as to maintain the expandable, inflatable bladder at a given position relative to a preselected portion of the spine.

12 Claims, 14 Drawing Figures

ORTHOPEDIC DEVICE

BACKGROUND OF THE INVENTION

1. Field of the Invention

This invention relates to an orthopedic device capable of providing ambulatory traction by being affixed to the torso or other specific regions of the human body and providing specifically directly pressures or forces to the spine area.

2. Description of the Prior Art

Numerous prior art devices exist which are particularly designed to exert pressures on various portions of the human body wherein such devices are portable and capable of being worn directly on the body of the patient while the patient is ambulatory. However, such devices are primarily designed to act as casts, splints, braces, etc. Such devices are especially adapted for immobilizing and/or protecting injured limbs or other parts of the anatomy. Such prior art braces, splints, etc., commonly include an inflatable structure which is positioned on the body for the purpose of exerting pressure thereon and thereby accomplishing the protective or immobilization features. Such prior art devices are demonstrated in the U.S. Pat. Nos. to Johnson, 3,955,565; Tourin, 3,786,805 and Sakita, 3,762,404. These devices, again, are primarily intended to exert pressure directly on predetermined portions of the body for the purpose of protection and/or immobilization.

The patents to Mildenberg, U.S. Pat. No. 1,646,590; Eisen, U.S. Pat. No. 3,071,133 and Shurtleff, U.S. Pat. No. 1,147,560 are directed to another type of "pressurized garment" in the form of massage apparatus belts or girdles which are inflatable and which are designed to exert pressure for the purpose of aiding muscle deficiency and fibrositis. It is contended that the design of such structures will improve low back ailments by providing cushioned support of the sacro-lumber region of the back, particularly during certain activities such as driving, which is believed to fatigue the back, etc.

Also, there are certain traction-applying devices in the form of truss structures as evidenced by the U.S. Pat. No. to Zumagelini, 3,667,457. Such a structure utilizes the inflation of certain cushions and/or spring members to accomplish the exertion of force between the head and the hips. In Zumagelini, pneumatic cushions are provided on the support for the head to be inflated so as to adjust the traction force exerted.

While the above set forth prior art devices accomplish their intended functions, there is still a need in the medical art for an orthopedic device capable of providing ambulatory traction through the application of pressure to various levels of the spine. More specifically, such a device would be of simple construction and design yet be capable, through the use of an inflated bladder, causing a ballooning effect, to enforce superior and inferior pressure, superior pressure, inferior pressure and posterior to anterior pressure on the lumbosacral, thoracic or cervical spine.

SUMMARY OF THE INVENTION

This invention is directed towards a portable orthopedic device generally in the form of a belt designed to surround the torso or other particular portion of the human body so as to properly position a traction means at various predetermined levels of the spine. The subject orthopedic assembly provides, as part of the traction means, a substantially rigid plate element which defines the base means of the traction means and an elastic, inflatable bladder securely attached thereto. A template plate, which is also made of substantially rigid material, is secured to the base plate and includes aperture means in the form of one or more apertures specifically designed and configured to allow protrusion of the bladder, when inflated, through one or more of the apertures in a predetermined direction. The direction of protrusion of the bladder as it "balloons" through one of the apertures determines the direction of force or traction provided to the specific area of the spine. In addition, the affixed base plate and template plate may have a specific longitudinal configuration to substantially correspond to predetermined curvatures of portions of the spine.

A support means is provided in which the base plate and template plate are mounted wherein the support means comprises a pocket structure secured to the belt like assembly so as to position the traction means adjacent the predetermined portion of the spine.

The subject orthopedic assembly makes use of the protruding elastic, inflatable bladder relative to the base plate and template plate being attached to the back surface of the belt assembly which in turn is applied to the lumbosacral region of the spine and the thoracolumbra section of the spine. One of the apparent features of the invention is the versatility of applying traction to the spine at specific levels with little or no discomfort. In addition, the simplicity of the apparatus enhances its use so that the garment may be worn under clothing without discomfort and with a negligible amount of weight while providing the desired traction to the predetermined regions or levels of the spine.

Forced air is provided to the inflatable bladder on either a continuous or intermittent basis by means of a substantially conventional pneumatic device such as the inflatable bulb apparatus commonly associated with sphygmomanometers.

Brace means is incorporated in the belt like structure of the subject assembly in the form of one or more substantially elongated strap elements. These strap elements are formed from substantially non-expandable material and are attached adjacent the traction means and/or pocket so as to provide proper resistance against displacement of the traction means when the bladder is inflated. Accordingly, the inflation of the bladder and resulting protrusion thereof through the apertures of the template plate causes pressure to be exerted, in a predetermined direction, upon the various levels of the spine. Dependent upon the specific configuration of the apertures and/or template plate and the position of the template plate relative to the level of the spine to be treated, the following types of pressures may be exerted thereon: superior to inferior traction, inferior pressure, superior pressure, posterior to anterior pressure and bilateral paravertebral pressure.

In operation, the appliance is placed on the patient's body and the bladder is inflated. Predetermined portions of the bladder will protrude through the various apertures formed in the template plate and thereby be forced into contact with the patient's body with a specific amount of pressure. The amount of pressure exerted is dependent upon the particular patient and the area and condition of the spine being treated. The pressure exerted by the predirected protrusions of the bladder serves to apply ambulatory traction to specific levels of the spine as indicated. Modification of the templates in terms of varying the dimension and configuration of the apertures formed therein will vary the protrusions. This in turn will cause a variance in pressure direction in an aid to the treatment of low back pain with specific conditions of the spine such as herniated discs, osteoarthritis, rheumatoid spondylitis, sciatic neuralgia, sacro-iliac myofascitis, acute spasm of bilateral paravertebral muscle masses, spinal nerve root irritation, specific and inflammatory processes of the spine, fractures, subluxations, dislocations and the like or any neuro-orthopedic correctual treatment utilizing the principles of traction. In addition, the principles of immobilization and trigger point principles in addition to mild soft tissue, manipulative therapy resulting in increased circulation and in decongestion are utilized.

By slowly enlarging the space between the vertebrae, through the application of the resulting traction in utilizing the appliance, the vertebrae in that space are separated and the pressure is removed enabling impingement and congestive processes to be relieved. As the patient begins walking, the vascular total flow is immediately increased, muscle spasm is diminished and the draining of inflammatory byproducts (exudates) is facilitated. The amount of pressure for this particular process to take place is most critical and may be controlled by the successive depression of the bulb or the release of pressure by the valve normally associated with such an inflation bulb. The bulb may then be removed or replaced for convenience while the belt structure of the appliance is worn by the patient.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
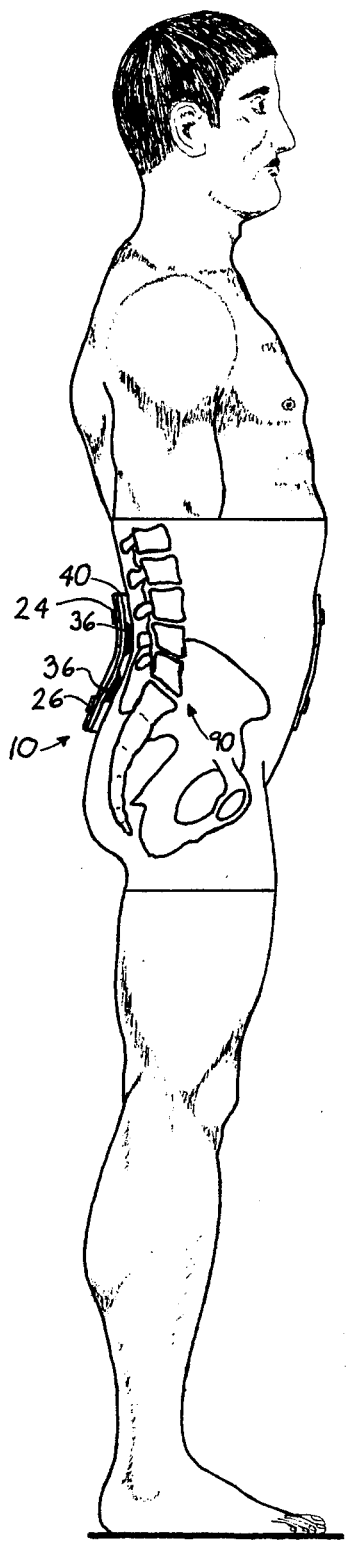
FIG. 1 is a side view done in schematic and partial cutaway showing the interior of the spinal section affected by the subject belt structure.
Figure 2:
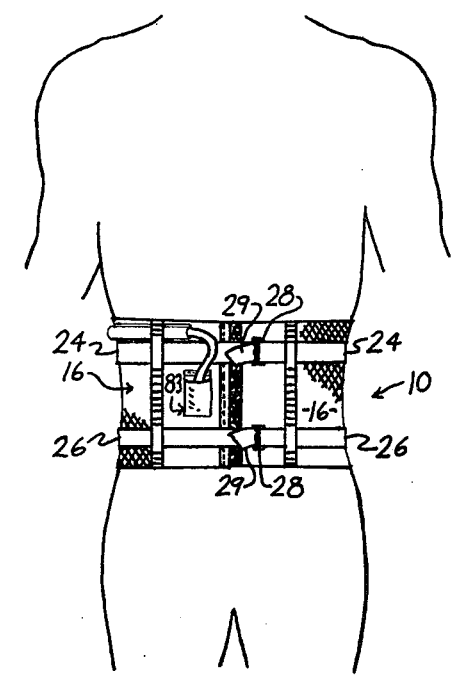
FIG. 2 is a schematic of a frontal section of a human wearer.
Figure 3:
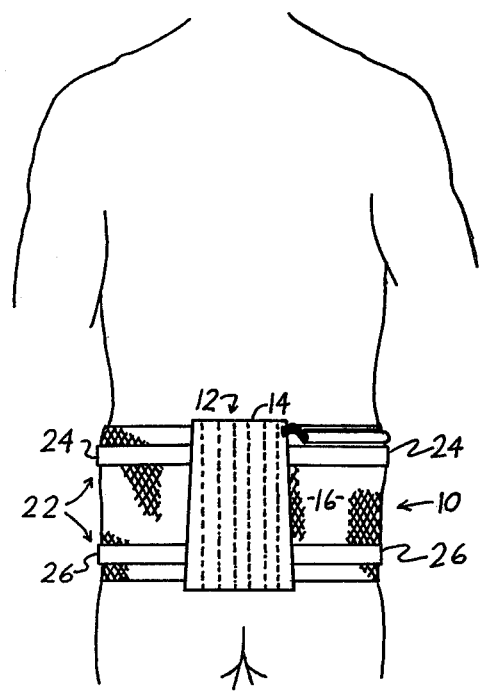
FIG. 3 is the embodiment of FIG. 2 showing the rear view of the belt in application.
Figure 4:
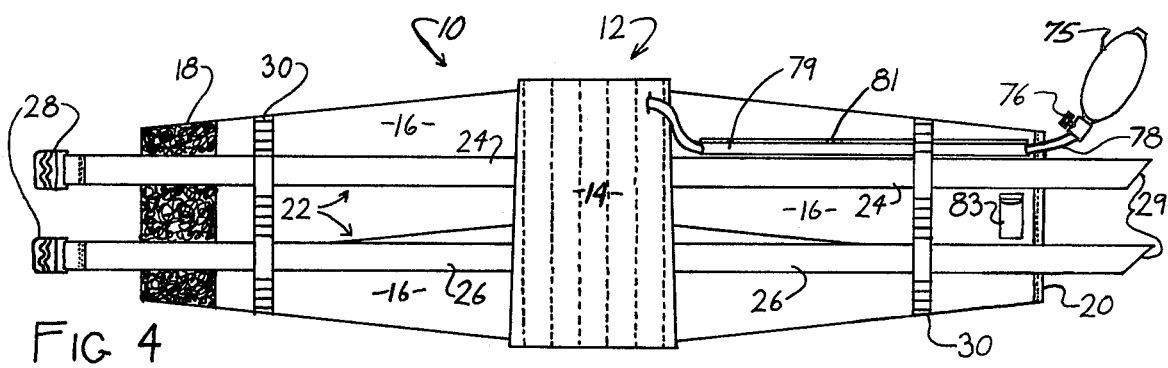
FIG. 4 is a rear view of the orthopedic appliance comprising a belt structure showing the supporting means in the form of a pocket element.
Figure 5:
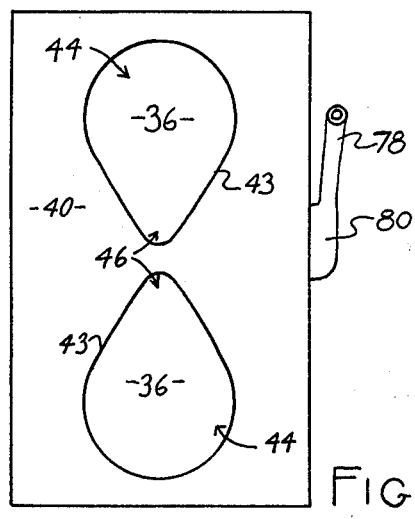
FIG. 5 is a front view showing one embodiment of the traction means of the present invention.
Figure 6:
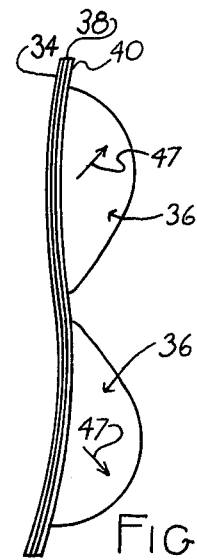
FIG. 6 is a side view of the embodiment of FIG. 5.

As shown primarily in FIGS. 1, 2 and 4, the orthopedic device of the present invention comprises a belt structure generally indicated as 10 designed to fit in substantially surrounding relation to the torso or other predetermined portions of the human body as indicated in FIGS. 1, 2, 3 and 4. More specifically, the belt structure 10 is designed to enable the traction means (FIGS. 5-14) to be positioned in a support means 12 in the form of a pocket 14. The disposition of the pocket 14 and, accordingly, the traction means is such as to dispose the traction means (to be described in greater detail hereinafter) adjacent predetermined portions of the spine (FIG. 3).

The belt structure itself comprises an elastic portion 16 which is expandable so as to accomplish complete surrounding relation to the body of the patient as well as provide a certain amount of additional pressure and support. Belt connecting means 18 and 20 are provided at opposite ends of the belt structure 10 and are specifically disposed for locking interconnection with one another. In the specific embodiment shown in FIG. 4, a velcro type fastener may be utilized so as to allow ready attachment and detachment of the connecting means 18 and 20 from one another and thereby facilitate removal of the belt.

Brace means generally indicated as 22 are mounted on the belt structure 10 and disposed in substantially adjacent, interconnecting relation to the pocket 14. The brace means comprises one or more strap elements 24 and 26 each having a substantially elongated configuration. The strap elements are connected at one end adjacent to or in actual engagement with the pocket means 14. The opposite ends constitute essentially free ends and include conventional connector elements 28 at one end thereof so as to accomplish securement of the opposite ends 29 thereto. Attachment means 30 are secured to the belt at various portions thereof to maintain the brace means or the strap elements 24 and 26 in proper place. It should be noted that while the portion 16 is essentially elastic to provide additional support to the torso or portions of the patient's body, the strap elements 24 and 26 are made from an essentially non-elastic or non-expandable material. This characteristic is provided so as to maintain the proper position of the pocket 14 and the traction means therein relative to the spine area and further to provide resistance against the pressure exerted by the bladder of the traction means as it is inflated.

With primary reference to FIGS. 5-14, the traction means of the present invention comprises a base 34 in the form of a substantially rigid plate having a flexible, substantially elastic material bladder 36 attached thereto. The bladder has its peripheral edges, as at 38, attached to the base plate 34 in secured fashion while the center portion of the bladder 36 is movable relative to the base plate 34 and is disposed so as to extend outwardly therefrom when inflated.

The traction means further comprises a template plate 40 fixedly secured to the base plate 34 and to a peripheral portion of the bladder as at 38. The general overall size and configuration of the template plate and the base plate are substantially the same and both are correspondingly configured to be housed or fitted within the pocket structure 14 comprising the support means 12. The template means or plate 40 is formed of a substantially rigid material and comprises aperture means generally indicated as 42. As set forth above, the specific configuration and dimension of the aperture means and the relative placement of the aperture means on the template plate 40 itself determines the directional force or pressure exerted by the inflated bladder. More specifically, in FIGS. 5 and 6 the aperture means comprises a plurality of apertures 43 disposed in spaced apart, substantially aligned relation to one another relative to the longitudinal axis of the plate. Each of the apertures comprises a first end generally indicated as 44 which has a substantially larger transverse dimension than the opposite end 46 of each aperture 42. This provides a substantially outward vector force capable of separating the various vertebrae affected so as to provide superior and inferior traction as indicated by directional arrows 47.

Figure 9:
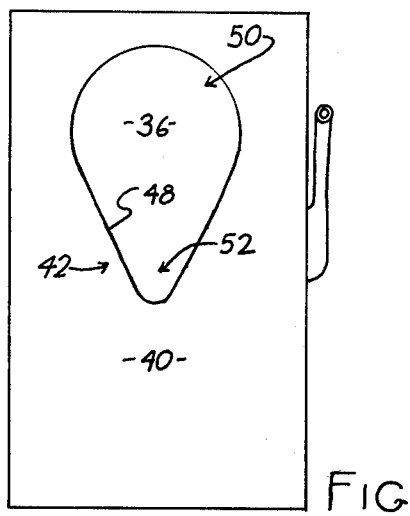
FIG. 9 is a front view of yet another embodiment of the traction means of the present invention.
Figure 10:
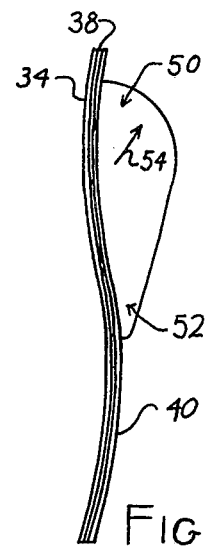
FIG. 10 is a side view of the embodiment of FIG. 9.

Similarly, in FIGS. 9 and 10 the aperture means 42 comprises a single aperture 48 having a first end 50 with a substantially greater transverse dimension than the opposite end generally indicated as 52. This particular embodiment provides a directional force as indicated by directional arrow 54 and is designated to provide superior pressure to the affected portions of the spine.

Figure 7:
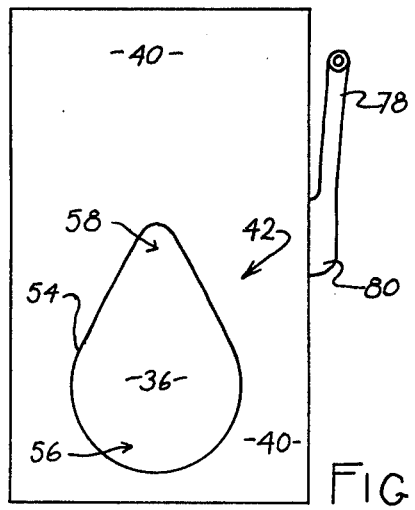
FIG. 7 is a front view of another embodiment of the traction means of the present invention.
Figure 8:
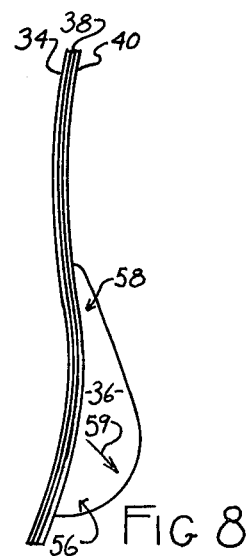
FIG. 8 is a side view of the embodiment of FIG. 7.

FIGS. 7 and 8 disclose an embodiment of the template plate 40 which includes aperture means 42 comprising a single aperture 54 having a first end 56 with a substantially greater transverse dimension than the opposite end 58. This provides pressure in the direction indicated by directional arrow 59. This provides inferior pressure to the particular vertebrae of the spine affected.

Figure 11:
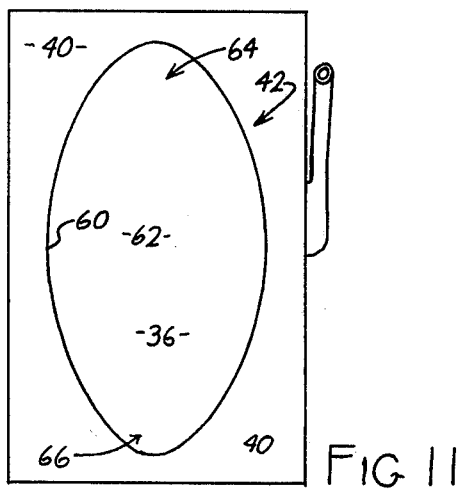
FIG. 11 is a front view of yet another embodiment of the traction means of the present invention.
Figure 12:
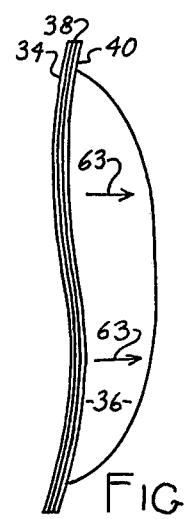
FIG. 12 is a side view of the embodiment of FIG. 11.

With reference to FIGS. 11 and 12, the aperture means 42 comprises a single, substantially elongated aperture 60 having a transverse portion generally indicated as 62 of greater dimension than either of the oppositely disposed ends 64 and 66. As shown in FIG. 9b, this provides pressure from the posterior to anterior direction as indicated by directional arrows 63.

Figure 13:
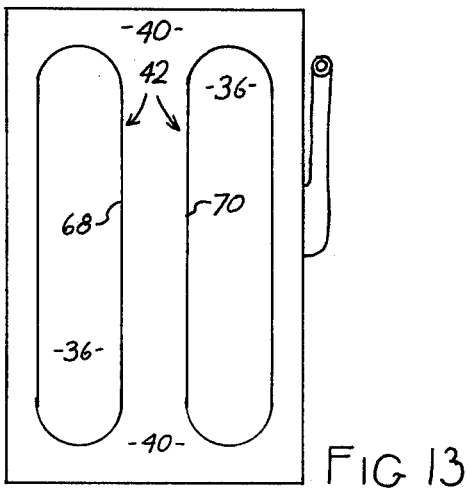
FIG. 13 is a front view of yet another embodiment of the traction means of the present invention.
Figure 14:
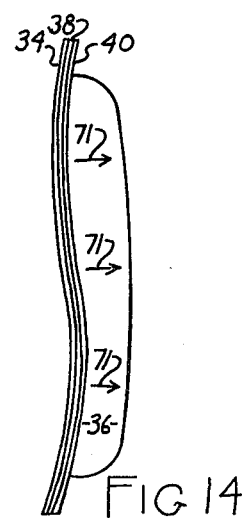
FIG. 14 is a side view of the embodiment of FIG. 13.

FIGS. 13 and 14 represent yet another embodiment of the present invention wherein the template plate 40 comprises a plurality of elongated side-by-side, spaced apart apertures 68 and 70 which define the aperture means 42. These apertures have a substantially uniform transverse dimension along their length and provide a bilateral paravertebral pressure in the direction substantially indicated by directional arrows 71. In each of the embodiments of FIGS. 5–14, the longitudinal, curvilinear configuration of the base plate and template plate itself are the same and may be adapted to substantially correspond to the curvilinear configuration of predetermined portions of the spine as indicated above.

Another structural feature of the present invention comprises the provision of an air pressure source generally in the form of an air inflatable bulb 75 of the type conventionally used in sphygmomanometers. A release valve 76 is provided so as to release pressure from the bladder through fluid conduit 78. Conduit 78 is joined to the bladder 36 by an integral or detachable junction 80 as shown. Fluid conduit 78 may be disposed on the belt structure in a desired position by sleeve 79. Sleeve 79 is securely attached to the belt as for instance along seam 81. Similarly, with regard to FIG. 2, an inclosure 83 may be used to secure bulb 75 to the belt or otherwise may be structured to house the cooperative end of the conduit and be attached in a manner to effect sealing the end thereof as shown.

With regard to FIG. 1, placement of the belt structure of the present invention is shown in operative relation to a wearer thereof. In the particular embodiment shown, the bladder 36 extends through two apertures in template 40 so as to put pressure on specific areas of the spine as at 90. This specifically disposed pressure serves to separate or more precisely impress upon the designated spinal portions, components of both inferior and superior pressures so as to separate the spinal portions and/or otherwise relieve pressure thereon as generally indicated.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. An orthopedic device of the type primarily designed to provide ambulatory traction to specific levels of the spine, said device comprising: belt means configured for attachment in substantially surrounding relation to a patient's body, said belt means including connecting means mounted adjacent opposite ends thereof, whereby said belt means may be removably attached to the patient; traction means secured to said belt means and disposed in pressure bearing relation to predetermined portions of the spine of the patient, support means secured to said belt means and supportingly engaging said traction means; said traction means comprising a base, an expandable bladder mounted on said base and disposed to extend outwardly therefrom in a predetermined direction, a template plate secured to said base on the opposite side of the bladder relative to said base, said template plate comprising aperture means formed therein and being specifically configured and dimensioned to define the primary direction of extension of said bladder therethrough, said bladder being secured in substantially sandwiched relation between said base and said template plate, each of said base and said template plate comprising substantially rigid material plate elements, said aperture means including at leat one aperture specifically dimensioned and configured to direct protrusion of said bladder therethrough in a predetermined direction and into a predetermined portion of the patient situated adjacent said orthopedic device, whereby force is exerted on predetermined portions of the body of the patient dependent upon the primary direction of the extension of said bladder through said template plate.

2. An orthopedic device as in claim 1 wherein said belt means comprises an elastic portion disposable in at least partially surrounding relation to the patient's body when said belt means is connected thereabout, whereby said elastic portion is disposed in support of the surrounded portion of the patient's body.

3. An orthopedic device as in claim 1 further comprising brace means connected to said belt means and comprising a substantially elongated construction extending along at least a major portion of the length of said belt means, said brace means formed from a substantially non-elastic material and secured adjacent said traction means and thereby maintaining said traction means into predetermined position relative to the spine of the patient.

4. An orthopedic device as in claim 3 wherein said brace means includes at least one strap element comprising two oppositely disposed free ends, each free end disposed adjacent a free end of said belt means and connectable to one another, whereby the position of said traction means is maintained in desired relation to the patient's spine.

5. An orthopedic device as in claim 4 wherein said brace means further comprises a plurality of strap elements disposed in at least partially spaced apart relation to one another and each comprising two oppositely disposed free ends each of which are in turn disposed adjacent a free end of said belt means and connectable to one another, whereby the position of said traction means is maintained in a desired relation to the patient's spine.

6. An orthopedic device as in claim 1 wherein said support means comprises a pocket structure secured to said belt means and configured and dimensioned to house said traction means therein, brace means attached to said pocket structure and disposed in surrounding relation to the patient when said belt means is secured thereto.

7. An orthopedic device as in claim 1 further comprising an air supply attached to said belt and disposed in fluid communication with said bladder, said bladder being formed from a substantially elastic material, whereby said bladder may be inflated a selected amount upon activation of said air supply.

8. An orthopedic device as in claim 1 wherein said aperture means comprises a plurality of apertures disposed in substantially aligned, spaced apart relation to one another relative to the longitudinal axis of said traction means, a first end of each aperture defined by a substantially greater transverse dimension than an opposite end of each of said apertures, said first end of each aperture disposed adjacent opposite ends of said template means.

9. An orthopedic device as in claim 1 wherein said aperture means comprises said one aperture having a first end including a substantially larger transverse dimension than the opposite end of said aperture, said one aperture being disposed closer to one end of said template plate than the opposite end of said template plate, and said first end of said aperture being disposed substantially adjacent to the peripheral edge of said template plate than the opposite end of said aperture, whereby said bladder protrudes through said one aperture in a substantially upward and outward direction.

10. An orthopedic device as in claim 1 wherein said one aperture comprises a substantially oblong configuration having a transverse dimension greater in the area of its midsection than at the opposing end thereof, whereby predetermined, desired pressure is exerted upon predetermined portions of the back in a preselected direction.

11. An orthopedic device as in claim 1 wherein said aperture means comprises a plurality of apertures each having a substantially elongated configuration and having correspondingly similar configurations and further being spaced apart from one another and extending substantially parallel to the longitudinal axis of the template plate.

12. An orthopedic device as in claim 1 wherein said base plate and said template plate are at least partially defined by a curvilinear configuration, said curvilinear configuration substantially corresponding to the curvature of predetermined portions of the human spine, whereby said bladder will extend outwardly from said base plate and template plate into engagement with predetermined portions of the patient's back.

* * * * *